US00PP28967P2

(12) United States Plant Patent
Benetka

(10) Patent No.: US PP28,967 P2
(45) Date of Patent: Feb. 20, 2018

(54) ***WEIGELA* PLANT NAMED 'VUKOZ041323'**

(50) Latin Name: *Weigela hybrida*
Varietal Denomination: VUKOZ041323

(71) Applicant: Vojtech Benetka, Chodov (CZ)

(72) Inventor: Vojtech Benetka, Chodov (CZ)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 15/330,183

(22) Filed: Aug. 18, 2016

(51) Int. Cl.
*A01H 5/02* (2006.01)

(52) U.S. Cl.
USPC ..... Plt./226

(58) Field of Classification Search
USPC ..... Plt./226
See application file for complete search history.

*Primary Examiner* — Anne M Grunberg
(74) *Attorney, Agent, or Firm* — Cassandra Bright

(57) ABSTRACT

A new and distinct *Weigela* plant named 'VUKOZ041323' is disclosed, characterized by rich flowering and re-blooming of white flowers with a yellow patch in the middle. It is also characterized as having light yellow flower buds. The new variety is a *Weigela*, normally produced as an outdoor garden plant.

3 Drawing Sheets

Latin name of the genus and species: *Weigela hybrida.*
Variety denomination: 'VUKOZ041323'.

BACKGROUND OF THE INVENTION

The new *Weigela* cultivar is a product of a planned breeding program conducted by the inventor, Vojtech Benetka, in Pruhonice, Czech Republic. The objective of the breeding program was to produce new *Weigela* varieties with white flowers. The cross resulting in this new variety was made in 2004.

The seed parent is an unpatented, unnamed proprietary *Weigela* referred to as '93-14-42'. The pollen parent is the unpatented, *Weigela* 'Volans'. The new variety was identified as a potentially interesting selection in 2008, at a research nursery in Pruhonice, Czech Republic.

Asexual reproduction of the new cultivar 'VUKOZ041323' by softwood cuttings was first performed in 2008, at a research nursery in Pruhonice, Czech Republic. Subsequent propagation has shown that the unique features of this cultivar are stable and reproduced true to type in five successive generations.

SUMMARY OF THE INVENTION

The cultivar 'VUKOZ041323' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'VUKOZ041323' These characteristics in combination distinguish 'VUKOZ041323' as a new and distinct *Weigela* cultivar:

1. White flowers with a yellow center.
2. Light yellow colored flower buds.

3. Rich flowering.
4. Re-blooming habit.

PARENT COMPARISON

Plants of the new cultivar 'VUKOZ041323' are similar to plants of the seed parent in most horticultural characteristics, however, plants of the new cultivar 'VUKOZ041323' differ in the following;

1. New cultivar has white flowers with a yellow center, whereas the parent has pure white flowers.

Plants of the new cultivar 'VUKOZ041323' are similar to plants of the pollen parent in most horticultural characteristics, however, plants of the new cultivar 'VUKOZ041323' differ in the following;

1. New cultivar has light yellow colored flower buds, whereas the parent has pinkish flower buds.

COMMERCIAL COMPARISON

Plants of the new cultivar 'VUKOZ041323' can be compared to the patented commercial variety *Weigela* 'Bokrasopea' (U.S. Plant Pat. No. 24,585). These varieties are similar in most horticultural characteristics; however 'VUKOZ041323' differs in the following:

1. New cultivar has white flowers with a yellow center whereas this comparator variety has white flowers with a slight yellow center which fades to light pink.
2. Flowers of the new cultivar have no major color change whereas the flowers of this comparator fade to light pink.

BRIEF DESCRIPTION OF THE PHOTOGRAPHS

The accompanying photograph in FIG. 1 illustrates in full color a side view perspective of a typical plant of 'VUKOZ041323' grown in a 1 gallon pot.

Figure 1:
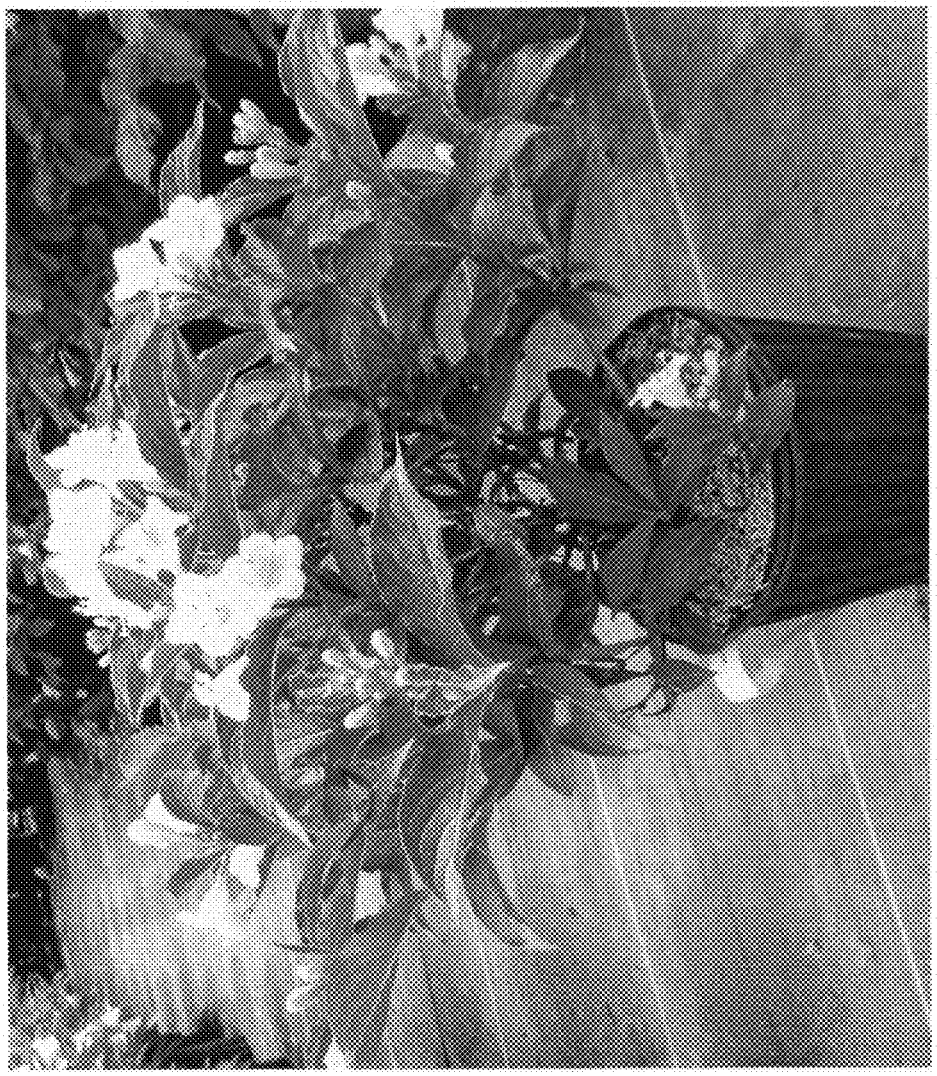
Figure 2:
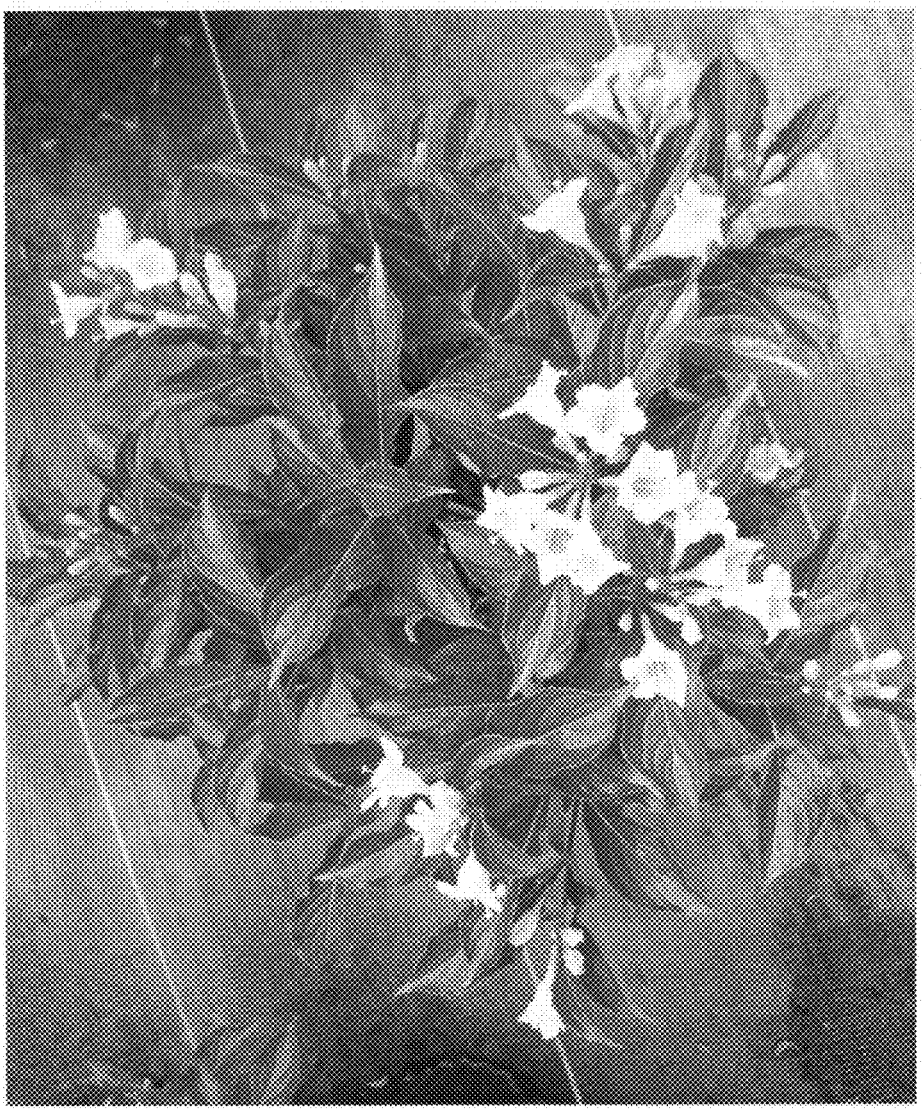
FIG. 2 illustrates the same plant with an overhead perspective. Age of the plant photographed is approximately 2 years.
Figure 3:
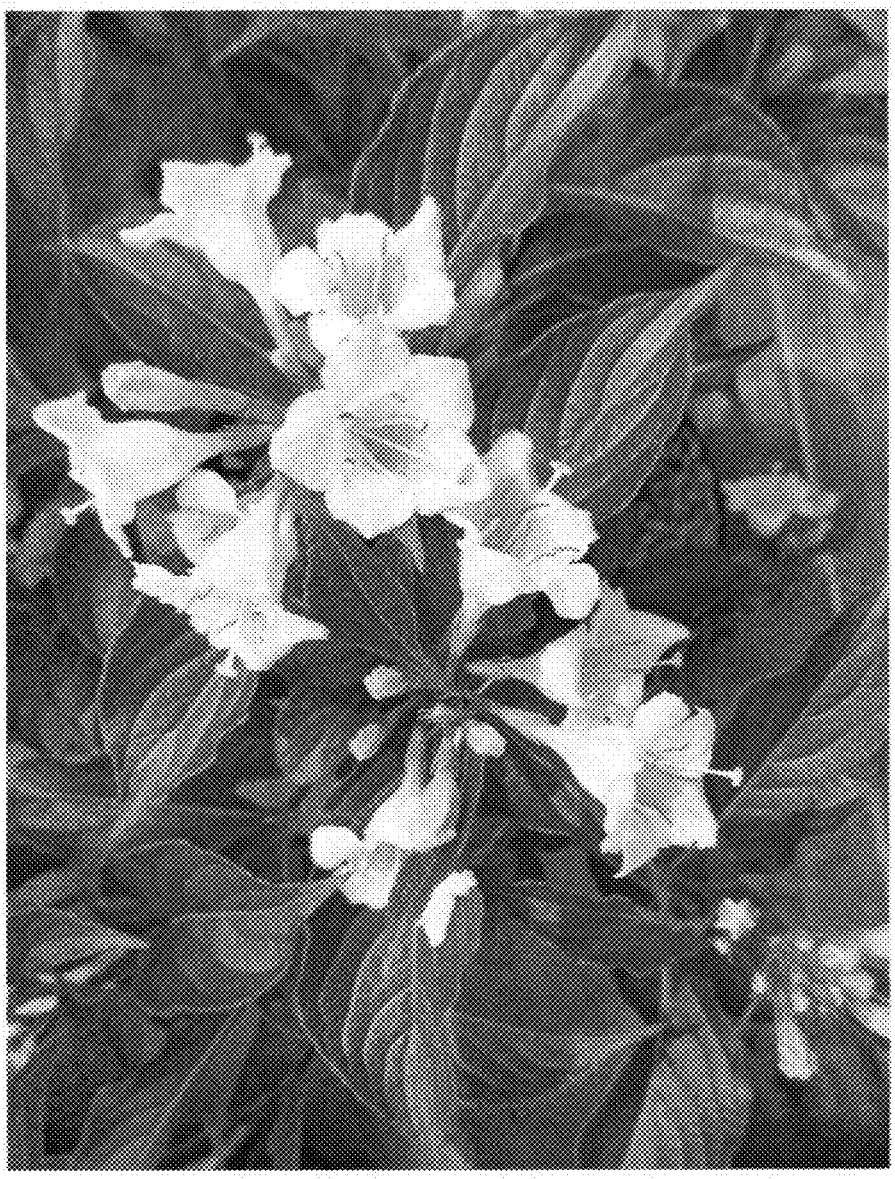
FIG. 3 illustrates a close-up view of the inflorescence and foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 1996 except where general terms of ordinary dictionary significance are used. The following observations and measurements describe 'VUKOZ041323' plants grown in a polyhouse in Grand Haven, Mich. Measurements were taken during late Spring. The plants were 2 years old. The growing temperature ranged from approximately 5° C. to 27° C. Measurements and numerical values represent averages of typical, plant types.

Botanical classification: *Weigela hybrida* 'VUKOZ041323'.

PROPAGATION

Time to initiate roots: Approximately 15 days.

Root description: Density is dense and freely branching. Thin root thickness. White in color, not effectively measured with a color chart.

Time to produce a rooted young plant: Approximately 60 days.

PLANT

Plant type: Shrub.

Age of plant described: Approximately 2 years old.

Growth habit: Compact growth with good branching.

Pot size of plant described: #2 container.

Overall plant shape: Upright and Rounded.

Height: 48.5 cm.

Plant spread: 82 cm.

Growth rate: Medium.

Plant vigor: Strong.

Branching characteristics: Opposite.

Length of primary lateral branches: 57 cm.

Diameter of lateral branches: 8.5 mm.

Quantity of lateral branches: 18.

Stem:

- *Stem appearance*.—Round.
- *Stem strength*.—Strong.
- *Aspect*.—40° to 45°.
- *Color*.—Near RHS Yellow-Green 145B blended with Brown 200D.
- *Pubescence*.—Yes.

Internode length: Range is 3.5 to 4.7 cm.

FOLIAGE

Leaf:

- *Arrangement*.—Opposite.
- *Leaf shape*.—Ovate-oblanceolate.
- *Average length*.—Approximately 7.2 cm.
- *Average width*.—Approximately 3.8 cm.
- *Apex*.—Acute.
- *Base*.—Acute to cuneate.
- *Margin*.—Serrulate.
- *Texture of top surface*.—Slight pubescence.
- *Texture of bottom surface*.—Pubescent, to a greater degree than upper surface.
- *Color*.—Young foliage upper side: Near RHS Green 137A. Young foliage under side: Near RHS Green 139C. Mature foliage upper side: Near RHS Green 137A. Mature foliage under side: Near RHS Green 139C.
- *Venation*.—Pattern: Pinnate. Color upper side: Near RHS Yellow-Green 145A. Color under side: Near RHS Yellow-Green 145B.
- *Petiole*.—Length: 7.0 mm. Diameter: 4.0 mm. Petiole color upper side: Near RHS Yellow-Green 145A. Petiole color lower side: Near RHS Yellow-Green 145B. Petiole Texture: Pubescent.
- *Foliage durability*.—Very durable.

FLOWER

Natural flowering season: Late spring to summer.

Inflorescence type and habit: Umbel to panicle.

Inflorescence height: 6.2 cm.

Inflorescence width: 5.0 cm.

Flower longevity on plant: Individual flowers approximately 2 weeks.

Quantity of flowers per inflorescence: 18 to 20.

Quantity of flowers per plant: Mature plant can have approximately 100 to 200 open flowers at one time.

Individual flowers:

- *Flower shape*.—Salverform.
- *Flower aspect*.—Upward and slightly outward.
- *Flowering arrangement*.—Single salverform flower.
- *Size*.—Diameter: Approximately 2.2 cm. Depth: Approximately 2.5 cm.
- *Flower other characteristics*.—Persistence: Self cleaning. Fragrance: Slight floral scent.

Bud:

- *Shape*.—Obovate-spatulate.
- *Length*.—2.6 cm.
- *Diameter*.—8.5 mm.
- *Color*.—Near RHS Yellow 2D.

Petal:

- *Petal arrangement*.—Whorled, fused at opening of throat.
- *Number of petals per flower*.—5.
- *Petal shape*.—Obovate to oblanceolate.
- *Petal base*.—Fused at throat.
- *Margin*.—Entire, slightly undulate.
- *Tip shape*.—Obtuse.
- *Length*.—1.0 cm.
- *Width*.—1.0 cm.
- *Texture*.—Upper: Smooth. Lower: Smooth.
- *Color*.—When opening: Upper side: Near RES White 155B. Under side: Near RHS White 155B. Fully open: Upper side: Near RHS White 155B. Under side: Near RHS White 155B. Fades to: Near RHS White 155B.
- *Flower tube*.—Length: 2.2 cm. Diameter, base: 2.0 mm. Color: Near RHS White 155B fading to near RHS Yellow-Green 145B and 145C.
- *Throat*.—Texture: Smooth. Color: Near RHS White 155B, bottom petal has a touch of near RHS Yellow-Orange 14A.

Sepal:

*Arrangement*.—Unguiculate, fused at base.
*Appearance*.—Long, narrowly triangular.
*Number*.—5.
*Shape*.—Narrowly triangular.
*Tip*.—Acute.
*Base*.—Obtuse.
*Margin*.—Entire.
*Length*.—8.0 mm.
*Width*.—1.0 mm.
*Texture, upper*.—Smooth, coriaceous.
*Texture, lower*.—Smooth, coriaceous.
*Color*.—Upper surface at maturity: Near RHS Yellow-Green 145B blending with near RHS Greyed-Purple 184B at the tip. Under surface at maturity: Near RHS Yellow-Green 145B blending with near RHS Greyed-Purple 184B at the tip.

Peduncle:

*Length*.—1.0 cm.
*Diameter*.—1.5 mm.
*Color*.—Near RHS Yellow-Green 145B.
*Orientation*.—Upright/outward.
*Strength*.—Good.
*Texture*.—Smooth, coriaceous, slightly pubescent.

Pedicel:

*Length*.—1.0 cm.
*Diameter*.—1.5 mm.
*Angle*.—Upright and outward.
*Strength*.—Good.
*Texture*.—Smooth, coriaceous, slightly pubescent.
*Color*.—Near RHS Yellow-Green 145B.

REPRODUCTIVE ORGANS

Stamens:

*Number*.—5.
*Filament length*.—2.2 cm.
*Filament color*.—Near RHS White 155B.

Anthers:

*Shape*.—Linear, slightly oblong.
*Length*.—5 mm.
*Color*.—Near RHS White 155B.
*Pollen color*.—Near RHS White 155B.
*Pollen amount*.—Some.

Pistil:

*Number*.—1 per flower
*Length*.—3.4 cm.
*Style*.—Length: 3.3 cm. Color: Near RHS White 155B.
*Stigma*.—Color: Near RHS Greyed-Yellow 160C. Shape: Globular, flat-bottomed.

OTHER CHARACTERISTICS

Seeds and fruits: Not observed to set fruit and seeds.

Disease/pest resistance: Neither resistance nor susceptibility to normal diseases and pests of *Weigela* have been observed, aside from mildew resistance.

Temperature tolerance: The new variety tolerates temperatures between −31° C. to 38° C.

Environmental stressors: Good resistance to wind and rain.

What is claimed is:

1. A new and distinct cultivar of *Weigela hybrida* plant named 'VUKOZ041323' as herein illustrated and described.

* * * * *